United States Patent [19]
Cooper et al.

[11] Patent Number: 5,746,924
[45] Date of Patent: May 5, 1998

[54] ANTIFOULANT FOR ACRYLONITRILE PURIFICATION

[75] Inventors: Fredrick L. Cooper, Houston; Piotr A. Kibala, Fulshear; Michael C. Weismiller, Sugar Land, all of Tex.

[73] Assignee: Nalco/Exxon Energy Chemicals, L.P., Sugar Land, Tex.

[21] Appl. No.: 838,120

[22] Filed: Apr. 15, 1997

[51] Int. Cl.$^6$ .................................................. C02F 5/10
[52] U.S. Cl. .......................... 210/698; 526/75; 558/462; 558/463
[58] Field of Search ................ 210/698; 526/75; 558/462, 463

[56] References Cited

U.S. PATENT DOCUMENTS

| | | |
|---|---|---|
| 3,876,508 | 4/1975 | Bonnema et al. ................ 558/466 |
| 4,264,476 | 4/1981 | Umemura et al. ................ 502/242 |
| 4,278,614 | 7/1981 | Umemura et al. ................ 558/322 |
| 4,545,943 | 10/1985 | Innes et al. ................ 558/326 |
| 4,609,502 | 9/1986 | Khoobiar et al. ................ 558/320 |
| 4,902,824 | 2/1990 | Syrinek ................ 560/248 |
| 5,091,093 | 2/1992 | Herwig et al. ................ 210/639 |

*Primary Examiner*—Neil McCarthy
*Attorney, Agent, or Firm*—Thomas M. Breininger; Robert A. Miller; Kelly L. Cummings

[57] ABSTRACT

The invention comprises a method of inhibiting the formation of foulants and residues, gums and precipitates, polymeric tars and other highly oxidized carbonaceous tars which can be formed in the process of manufacture and recovery of acrylonitrile. The method comprises adding to the liquid or gaseous phases passing through, or stored in acrylonitrile process equipment, an effective antifouling amount of a dispersant which is stable in the environment within an acrylonitrile process and is neutral to the equipment used for the manufacture of acrylonitrile.

9 Claims, No Drawings

ANTIFOULANT FOR ACRYLONITRILE PURIFICATION

BACKGROUND OF THE INVENTION

1. Field of the Invention

The invention relates to a method of dispersing foulants which are generated in an acrylonitrile production unit.

2. Description of the Prior Art

The use of dodecylbenzene sulfonic acid containing products as antifoulants and dispersants in a vinyl acetate monomer production process is disclosed in U.S. Pat. No. 4,902,824 issued to Allen Syrinek, the disclosure of which is incorporated herein by reference. The '824 patent claims the use of benzene sulfonic acids in solvents as antifoulants for the vinyl acetate manufacturing process.

Similar fouling problems occur in other production processes, as well. Although many hydrocarbon production processes are superficially similar, it is often the case that compositions which are effective for a given application in one process are totally unsuitable in another. As exemplified in the instant application, the fact that benzene sulfonic acids effectively disperse foulant in the vinyl acetate manufacturing process, is not dispositive of whether benzene sulfonic acids would also disperse foulant in acrylonitrile manufacturing processes. The nature of the monomers and of the fouling species in these areas are very different as described below.

FOULING SPECIES

Vinyl Acetate Manufacturing poly(vinyl acetate), vinyl acetate oligomers, polymeric aldehydes, oxidation products Acrylonitrile Manufacturing poly(acrylic acid)

poly(acrylamide)

poly(acrylonitrile)

MECHANISMS OF FOULANT FORMATION

Vinyl Acetate Foulant

Poly(vinyl acetate) and the vinyl acetate oligomers are formed by the free radical polymerization of vinyl acetate. Vinyl acetate dimers are formed by the addition of acetic acid across the carbon-carbon double bond of vinyl acetate. Aldol condensation of the aldehyde species result in oligomers and polymers. Other polymers related to the ethylene oxidation in the reactor section can also contribute to the acetic acid tower fouling.

Acrylonitrile Foulant

Poly(acrylonitrile), poly(acrylamide), and poly(acrylic acid) are formed by the free radical polymerization of acrylonitrile, acrylamide, and acrylic acid respectively. Acrylamide and acrylic acid are the products of the hydrolysis of acrylonitrile. It is not known whether the hydrolysis occurs before or after the polymerization.

FOULANT SOLUBILITIES

Poly(vinyl acetate) is soluble in vinyl acetate.

Poly(acrylonitrile) is not soluble in acrylonitrile.

The following tables list solvents and nonsolvents for poly(vinyl acetate) and poly(acrylonitrile). Poly(vinyl acetate) is soluble in common organic solvents. Poly(acrylonitrile) is soluble in relatively exotic solvents, but not in the more common hydrocarbon solvents or water. The solvents for poly(vinyl acetate) have dipole moments in the range of 0–2 D. The solvents for poly(acrylonitrile) have dipole moments in the range of 0–4.3 D.

| Solvents For Polymers of Vinyl Acetate and Acrylonitrile | |
|---|---|
| poly(vinyl acetate) solvents | poly(acrylonitrile) solvents |
| 2,4-dimethyl-3-pentanol | 1,1,1-trichloro-3-nitro-2-propane |
| allyl alcohol | 2-hydroxyethyl methyl sulfone |
| benzene | 2-oxazolidone |
| acetone | 4-nitrophenol |
| acetic acid | 1,3,3,5-tetracyanopentane |
| benzyl alcohol | N,N-dimethyl-$\alpha,\alpha,\alpha$-trifluoroacetamide |
| carbon tetrachloride/ethanol | acetic anhydride |
| chlorobenzene | bis(2-cyanoethyl)ether |
| chloroform | bis(4-cyanobutyl)sulfone |
| dichloroethylene/ethanol 20:80 | chloroacetonitrile |
| dioxane | chloroacetonitrile/water |
| ethanol/water | cyanoacetic acid |
| glycol ether esters | dimethyl sulfone |
| glycol ethers | dimethyl phosphite |
| lower aliphatic esters | dioxanone |
| methanol | DMA |
| tetrahydrofurfuryl alcohol | DMF |
| THF | DMSO |
| toluene | $\epsilon$-caprolactam |
|  | ethylene carbonate |
|  | ethylene oxalate |
|  | fumaronitrile |
|  | $\gamma$-butyrolactone |
|  | hydroxyacetonitrile |
|  | maleic anhydride |
|  | malonitrile |
|  | methylene dithiocyanate |
|  | nitric acid |
|  | N-formylhexamethyleneimine |
|  | N-methyl-$\beta$-cyanoethylformamide |
|  | N-nitrosopiperidine |
|  | nitromethane/water (94:6) |
|  | phenylene diamines |
|  | sulfuric acid |
|  | tetramethylene sulfoxide |

| Nonsolvents For Polymers of Vinyl Acetate and Acrylonitrile | |
|---|---|
| poly(vinyl acetate) nonsolvents | poly(acrylonitrile) nonsolvents |
| saturated hydrocarbons | hydrocarbons |
| mesitylene | chlorinated hydrocarbons |
| carbon tetrachloride | alcohols |
| ethanol (anhydrous) | diethyl ether |
| ethylene glycol | ketones |
| cyclohexanol | 3,4-dimethyl sulfolane |
| diethyl ether | 1,6-hexanediamine |
| higher esters C > 5 | propyl formate |
| carbon disulfide | formamide |
| water | DMF |
| dilute acids | diethylformamide |
| dilute alkalies | methoxyacetamide |
|  | dimethyloxamide |
|  | ethylene urea |
|  | acetonitrile |
|  | acrylonitrile |
|  | methoxyacetomitrile |
|  | 1-hydroxypropionitrile |
|  | dimethylmalonitrile |
|  | 1,1-dimethylsuccinonitrile |
|  | methyl thiocyanate |
|  | hexamethylene dithiocyanate |
|  | aliphatic nitro-compounds |
|  | 1-nitrophenol |
|  | diethyl sulfoxide |
|  | bis(2-hydroxyethyl) sulfoxide |
|  | diethyl sulfone |

The foulant species for each process are different. Poly(vinyl acetate) is soluble in its monomer. Poly(acrylonitrile) is not. Foulant in the vinyl acetate process can result from addition across the carbon-carbon double bond of the monomer molecule. This does not occur in the acrylonitrile process.

In summary, the foulant species in the vinyl acetate and acrylonitrile processes exhibit different physical characteristics. These differences include physical properties, solubilities and reactivities. The interaction of dispersants with foulant material is dependent on properties like polarity (which correlates with dipole moment) and solubility. Thus, the fact that dodecylbenzene sulfonic acid effectively disperses poly(vinyl acetate), does not predict that it will effectively disperse poly(acrylonitrile), a material that has considerably different solubility characteristics.

It would therefore be an advance in the art if one could simply add an effective amount of an antifoulant to such acrylonitrile process equipment, so as to minimize or eliminate the possibility of such foulants forming and inhibiting the ability to achieve maximum use of the acrylonitrile process equipment.

SUMMARY OF THE INVENTION

The invention comprises a method of inhibiting the formation of foulants and residues, gums and precipitates, polymeric tars and other highly oxidized carbonaceous tars which can be formed in the process of manufacture and recovery of acrylonitrile. The method comprises adding to the liquid or gaseous phases passing through, or stored in acrylonitrile process equipment, an effective antifouling amount of a dispersant which is stable in the environment within an acrylonitrile process and is neutral to the equipment used for the manufacture of acrylonitrile.

DESCRIPTION OF THE PREFERRED EMBODIMENTS

The dispersant which has been found that meets all of these requirements, i.e., a dispersant that can inhibit the fouling caused by polymeric tars, residues, highly oxidized carbonaceous tars and debris, and similar foulants as described above, while being compatible with the environment and chemicals used to manufacture acrylonitrile, without causing difficulties in the manufacture of such monomer, are primarily those dispersants which are alkyl sulfonic acids. These alkyl sulfonic acids are exemplified by such materials as dodecylbenzene sulfonic acid, dioctyl sulfosuccinic acid, and similar materials, such as methane sulfonic acid and the like. These sulfonic acids may be used as is, or may be formulated in a compatible solvent, and may include, optionally, other dispersants, other surfactants, anti-foaming agents corrosion inhibitors, and similar ingredients.

The antifoulant formulation preferably used is one that contains dodecylbenzene sulfonic acid, and/or its salts, optionally admixed and/or dissolved in an organic polar solvent, such a butyl cellosolve, an alkyl capped diether material available in commerce.

These antifoulants can contain from about 1 to about 100 weight percent alkyl sulfonic acid, preferably dodecylbenzene sulfonic acid, and/or its salts, admixed and/or dissolved in a polar solvent, such a butyl cellosolve, an alkyl capped diether material available in commerce.

In addition, the dodecylbenzene sulfonic acid may be present as its salts, particularly its quaternary ammonium or amine salts by neutralizing the sulfonic acid with various bases or with various amines, including polyamines and the like.

In addition to the dodecylbenzene sulfonic acid, other hydrocarbonaceous sulfonic acids may be used in the invention. These sulfonic acids may be alkyl sulfonic acids which can include, but are not limited to, such organic sulfonic acids as toluene sulfonic acid, methane sulfonic acid, dodecyl sulfosuccinic anhydride, dodecyl sulfosuccinic acid, and dioctyl sulfosuccinate. Representative of these sulfonic acids are those having the structure:

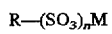

$$R\text{---}(SO_3)_n M$$

wherein R is a hydrocarbonaceous group chosen from linear or branched alkyl groups, aromatic, cyclic, alkaryl, aralkyl, or alkenyl groups, and mixtures thereof; M is H, alkali metals, alkaline earth metals, ammonium cations, alkylamine cations, quaternary amine cations, and the like, or mixtures thereof; and n ranges from about 1 to about 6, preferably between about 1–4, and most preferably is 1–2.

Also included in such effective sulfonic acids are structures which include alkyl aromatic sulfonic acids or alkyl naphthenic sulfonic acids, as will be described in detail hereafter.

The organic polar solvents (protic and aprotic) to be used are solvents such as butyl cellosolve or any of the ethylene oxide based cellosolve capped ether solvents, and may also include such organic polar solvents as the diethyl ether of tetraethylene glycol, polyethylene and polypropylene oxide alkyl ethers, and generally may also include other ether solvents, such as diethyl ether. In addition, other polar solvents that also function include certain organic acids, such as acetic acid, or such other polar solvents such as diacetone alcohol, linear alkyl and branched alkyl alcohols, such as methanol, ethanol, propanol, isopropanol, t-butyl alcohol, and the like. Admixtures of these polar solvents may also be used.

Many more common solvents may also be used effectively with the claimed invention; esters, such as ethyl acetate, ketones, such as acetone, nitrites, such as acetonitrile and acrylonitrile, water (when blended with some of the above solvents), and admixtures of the above solvents.

Also included are aliphatic and aromatic hydrocarbon solvents, dimethylacetmide (DMAC), dimethylformamide (DMF), dimethyl sulfoxide (DMSO), and heavy aromatic naphtha.

The alkyl sulfonic acids described above are preferred when used in process streams at concentrations ranging from about 1 ppm to about 20,000 ppm, based on the weight ratios of the additive formulation to the process stream to which the formula is added. However, hydrocarbonaceous sulfonic acids, or their formulations can function as antifoulants at treatment concentrations ranging from about 1–20,000 ppm, preferably between about 5–1000 ppm, and most preferably, between about 10–100 ppm (wt. %) treatment acid based on the process stream being treated.

Also, as can be seen, although the alkyl sulfonic acids can be used as amine salts, the activities of some amines, such as the heavy amine condensate salts are not as good as the activities of the free acids. Therefore, it is most preferred to use the sulfonic acids of the instant invention as the free acid.

The following examples are presented to describe preferred embodiments and utilities of the invention and are not meant to limit the invention unless otherwise stated in the claims appended hereto.

EXAMPLE 1

A sample of fouling deposit was obtained from a fouled acrylonitrile plant cooler. The deposit sample was ground together with dimethyl sulfoxide (DMSO) and the resulting suspension was filtered through 0.45 μm filter. The dark brown filtrate (saturated solution of the foulant) was used for dispersion testing. 15 mL of organic layer separated from heads bottoms stream (also obtained from an acrylonitrile plant) was placed in a conical test tube and was treated with 100 μL of the filtrate solution. Immediately, solid material precipitated from the solution. This tube was labeled A. Another tube, labeled B, was filled with 15 mL of organic layer separated from heads bottoms stream and 100 μL of the filtrate solution. This tube was treated with 50 ppm of the material of the invention. Both tubes were capped, shaken for a few minutes, and observed. Within minutes a solid material precipitated to the bottom of tube A. No such material was observed in tube B. The tube stayed homogeneous and precipitate free—the fouling material in tube B remained suspended in the solution.

EXAMPLE 2

The organic layer separated from heads bottoms was added to three graduated centrifuge tubes. The tubes were labeled C, D, and E. Tube C was treated with the material of the invention. Tubes D and E were not treated with the material of the invention. The foulant solution was added to each tube to simulate the introduction of acrylonitrile fouling material. Tube C remained homogeneous and precipitate free. Tubes D and E displayed insoluble material which precipitated to the bottom of the tubes within a short time period. Tube C was subsequently treated with material of the invention. The tube was capped, shaken, and observed. After a short time period, tube E approached the quality of tube C, which was homogeneous and precipitate free. Thus, the material of the invention increased the dispersity of the fouling material within the acrylonitrile matrix prior to the foulant precipitation and after the foulant precipitation.

EXAMPLE 3

Tubes C and D from Example 2 were evaluated at temperature extremes to determine the performance stability of the material of the invention. The temperature range of interest was from 8° C. (46° F.) to 80° C. (176° F.). Tube C remained homogeneous and precipitate free throughout the temperature range of interest.

Changes can be made in the composition, operation and arrangement of the method of the present invention described herein without departing from the concept and scope of the invention as defined in the following claims:

We claim:

1. A method of inhibiting the formation of tars, gums, and foulants in acrylonitrile monomer process equipment which comprises adding to the liquid or gaseous phases contained therein an effective antifouling amount of an antifoulant, said antifoulant having the structure:

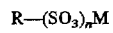

$$R-(SO_3)_n M$$

wherein R is a hydrocarbonaceous group having from 1–34 carbon atoms chosen from linear or branched alkyl groups, aromatic, cyclic, alkaryl, aralkyl, or alkenyl groups, alkyl diphenyl ether groups, dialkyl naphthalene groups, or mixtures thereof; M is chosen from the group consisting of H, alkali metals, alkaline earth metals, ammonium cations, alkyl ammonium cations, or mixtures thereof, and n ranges from 1 to about 6.

2. The method of claim 1 wherein the antifoulant is selected from the group consisting of dodecylbenzene sulfonic acid, methyl sulfonic acid, toluene sulfonic acid, alkyldiphenyl ether disulfonic acid, dialkyl naphthalene sulfonic acid, dioctyl sulfosuccinic acid, and mixtures thereof.

3. The method of claim 1 wherein the antifoulant is admixed with an organic polar solvent selected from the group consisting of alcohols, ethers, esters, ketones, nitriles or mixtures thereof.

4. The method of claim 1 wherein the effective antifouling amount of antifoulant ranges between about 1–20,000 parts per million antifoulant, based on the process stream being treated.

5. The method of claim 4 wherein the effective amount of antifoulant ranges between about 5–1000 parts per million.

6. The method claim 5 wherein the effective amount ranges from about 10–100 parts per million antifoulant.

7. The method of claim 1 wherein the antifoulant is admixed with a polar solvent selected from the group consisting of acetic acid, diacetone alcohol, dimethylacetmide (DMAC), dimethylformamide (DMF), dimethyl sulfoxide (DMSO), water and mixtures thereof.

8. The method of claim 1 wherein the antifoulant is admixed with a solvent selected from the group consisting of aliphatic and aromatic hydrocarbons and mixtures thereof.

9. The method of claim 3 wherein the organic polar solvent is admixed with water.

* * * * *